(12) United States Patent
Park et al.

(10) Patent No.: US 6,476,257 B1
(45) Date of Patent: Nov. 5, 2002

(54) METHOD FOR PREPARING AROMATIC CARBOXYLIC ACIDS FROM ALKYLAROMATICS BY LIQUID-PHASE OXIDATION

(75) Inventors: Sang-Eon Park, Daejeon (KR); Jin S. Yoo, Flossmoor, IL (US); Ki-Won Jun; David B. Raju, both of Daejeon (KR); Young-Ho Kim, Choongchungbook-do (KR)

(73) Assignee: Korea Institute of Chemical Technology (KR)

( * ) Notice: Subject to any disclaimer, the term of this patent is extended or adjusted under 35 U.S.C. 154(b) by 0 days.

(21) Appl. No.: 09/964,750

(22) Filed: Sep. 28, 2001

(30) Foreign Application Priority Data

Mar. 31, 1972 (KR) .............................................. 01-17072

(51) Int. Cl.⁷ ........................ C07C 51/16; C07C 51/255
(52) U.S. Cl. ...................... 562/412; 562/412; 562/413; 562/414
(58) Field of Search ................................ 562/412, 413, 562/414

(56) References Cited

U.S. PATENT DOCUMENTS

| 2,245,528 | A |   | 6/1941  | Loder et al.        |
|-----------|---|---|---------|---------------------|
| 2,833,816 | A |   | 5/1958  | Saffer et al.       |
| 3,890,374 | A | * | 6/1975  | Fujii et al.        |
| 4,258,209 | A | * | 3/1981  | Hanotier et al.     |
| 4,786,753 | A |   | 11/1988 | Partenheimer et al. |
| 5,041,633 | A |   | 8/1991  | Partenheimer et al. |
| 5,081,290 | A |   | 1/1992  | Partenheimer et al. |
| 5,693,856 | A | * | 12/1997 | Ramachandran et al. |

FOREIGN PATENT DOCUMENTS

| KR | 2000-0041505 | 7/2000  |
| KR | 2000-0041507 | 7/2000  |
| KR | 2000-0067444 | 11/2000 |

* cited by examiner

*Primary Examiner*—Johann Richter
*Assistant Examiner*—Farhad Forohar
(74) *Attorney, Agent, or Firm*—Finnegan, Henderson, Farabow, Garrett & Dunner, L.L.P.

(57) ABSTRACT

The present invention relates to a method for preparing aromatic carboxylic acid from alkylaromatics by liquid-phase oxidation. More particularly, the present invention relates to a method for preparing aromatic carboxylic acid from alkylaromatics by oxidation in acetic acid as solvent with oxygen-containing gas in the presence of cobalt/manganese/bromine complex catalyst, wherein nickel and carbon dioxide in an appropriate amount are added to increase an activity of cobalt/manganese/bromine complex catalyst. Especially nickel has a synergistic effect with carbon dioxide and maximize the to formation of the desired product having the corresponding carboxylic groups to the number of alkyl groups in a reactant.

8 Claims, No Drawings

METHOD FOR PREPARING AROMATIC CARBOXYLIC ACIDS FROM ALKYLAROMATICS BY LIQUID-PHASE OXIDATION

BACKGROUND OF THE INVENTION

Field of the Invention

The present invention relates to a method for preparing aromatic carboxylic acids from alkylaromatics by liquid-phase oxidation. More particularly, the present invention relates to a method for preparing aromatic carboxylic acids from alkylaromatics by oxidation in acetic acid as solvent with oxygen-containing gas in the presence of cobalt/manganese/bromine complex catalyst, wherein nickel and carbon dioxide are added in an appropriate amount to increase an activity of cobalt/manganese/bromine complex catalyst. Especially nickel has a synergistic effect with carbon dioxide and maximize the formation of the desired product having the corresponding carboxylic groups to the number of alkyl groups in a reactant.

The first liquid-phase oxidation in place of vapor-phase oxidation used in a preparation of aromatic carboxylic acid was introduced in U.S. Pat. No. 2,245,528 to perform at 100–320° C. under the pressure to keep a saturated fatty acid solvent in liquid state and in the presence of metal catalyst having several valances. An activity was the most with cobalt among metals and accelerated by adding ketones or aldehydes. However, this method converts only one alkyl group of mono-, di-, or trimethyl benzene to benzene monocarboxylic acids such as benzoic acid, toluic acid, and dimethyl benzoic acid.

Other liquid-phase oxidations of alkyl aromatics at an elevated temperature and pressure and in the presence of catalyst have been disclosed to convert all the alkyl groups to the corresponding carboxylic acids. Used catalysts are combinations of bromine and transition metals, especially use of cobalt/manganese/bromine complex catalyst in the oxidation of p-xylene to terephthalic acid (U.S. Pat. No. 2,833,816). Further, preparations of benzene di or tricarboxylic acid from di or trimethyl benzene such as p-xylene, m-xylene or pseudocumene (1,2,4-trimethyl benzene) by oxidation have been developed and widely commercially applied (U.S. Pat. Nos. 5,041,633 and 5,081,290). The prepared aromatic carboxylic acids after purified have been using as raw materials to produce polyesters, fibers, films and the like.

However, the use of cobalt/manganese/bromine complex catalyst has some drawbacks in side-reactions, expensive cost, difficulties in treatment and sedimentation. Since reduced reaction time to produce aromatic carboxylic acids will ensure an improvement of productivity and manufacturing cost, development of efficient catalysts and processes has been constantly progressing. Even now, there is no better catalyst than cobalt/manganese/bromine complex catalyst.

Development has been continued to improve an activity of a catalyst by adding other components. Nickel has been used in liquid-phase oxidation of dimethyl benzene or pseurocumene with molecular oxygen but cobalt was not added (U.S. Pat. No. 4,786,753). Nickel has been also used in liquid-phase oxidation of p-xylene with peroxide in the presence of cobalt/manganese/bromine complex catalyst (KR Patent 2000-41505) but the activity was worse than that of cobalt/manganese/bromine complex catalyst.

On the other hand, since liquid-phase oxidation of alkyl aromatics in the presence of a stoichiometric excess of oxygen- or highly pure oxygen-containing gas is susceptible to explosion for formation of flammable gas, carbon dioxide is used to reduce a risk of flammability or explosion. It is further known that it does not affect the activity of the reaction (U.S. Pat. No. 5,693,856 and EP Patent 0785183 A2). Recently carbon dioxide has been used with cobalt/manganese/bromine complex catalyst (KR Patent Publication 2000-67444) and additionally with alkali metal or alkali earth metal (KR Patent Publication 2000-41507) to improve the reaction efficiency in the preparation of aromatic carboxylic acid via liquid-phase oxidation. However, the development of metal or non-metal component to be combined optimally with carbon dioxide is highly demanded to improve the reaction efficiency largely.

SUMMARY OF THE INVENTION

The present invention has been completed with the development of optimal combination of carbon dioxide and nickel, which exhibits synergistic effect, in the preparation of aromatic carboxylic acids by liquid-phase oxidation in the presence of cobalt/manganese/bromine complex catalyst to remarkably improve reaction efficiency due to increase in the reaction rate of the oxidation.

An object of the present invention is to provide a method for preparing aromatic carboxylic acids, which is highly efficient in the presence of commercial cobalt/manganese/bromine complex catalyst with carbon dioxide and nickel.

DETAILED DESCRIPTION OF THE INVENTION

In the preparation of aromatic carboxylic acids by liquid-phase oxidation of alkylaromatics and partially oxidized intermediates with oxygen-containing gas in the presence of cobalt/manganese/bromine complex catalyst and in acetic acid as the solvent, the present invention is characterized in that nickel and carbon dioxide are used in the preparation of aromatic carboxylic acids. Especially, nickel and carbon dioxide enhance each other's promotional effect, showing namely synergistic effect.

The present invention is described in detail as set forth hereunder.

The present invention uses an appropriate amount of carbon dioxide and nickel in the conventional liquid-phase oxidization of alkylaromatics which is performed by using oxygen-containing gas in the presence of cobalt/manganese/bromine complex catalyst and in acetic acid as the solvent to produce aromatic carboxylic acids, thus provides some advantages in that the reaction efficiency with increases in the reaction rate and reaction temperament is highly improved, and the selectivity toward the product polycarboxylic acids is largely increased due to a sharp decrease in the formation of partial oxidized intermediates.

The present invention is described in more detail in accordance with addition components and reaction conditions as set forth hereunder. The addition components are alkylaromatics, oxygen-containing gas, cobalt/manganese/bromine complex catalyst, and reaction activators of nickel and carbon dioxide.

The alkylaromatics are the aromatic compounds having at least one alkyl group. Examples are toluene, o-xylene, m-xylene, p-xylene, pseudocumene (1,2,4-trimethylbenzene), mesitylene (1,3,5-trimethylbenzene), durene (2,3,5,6-tetramethylnaphthalene), methylnaphthalene, 2,6-dimethylnaphthalene, 4,4'-dimethylbiphenyl and an intermediate thereof. These alkylaromatic compounds are converted to the corresponding aromatic carboxylic acids, benzoic acid, phthalic acid, isophthalic acid, terephthalic acid, trimellitic acid, trimesic acid, pyromellitic acid, carboxylnaphthalic acid, 2,6-dicarboxynaphthalic acid and 4,4'-dicarboxybiphenylic acid.

It is prefer to use manganese/cobalt in the atomic weight ratio range of 0.1–5, preferably 0.5–3 in cobalt/manganese/bromine complex catalyst. It is further prefer to use bromine/(manganese+cobalt) in the atomic weight ratio range of 0.1–5, preferably 0.5–2. Cobalt is used 50–10,000 ppm relative to the total amount of reactants, preferably 100–1,000 ppm. Any bromine compound such as HBr, $Br_2$, tetrabromoethane and benzyl bromide may be used as a source of bromine. As sources of manganese and cobalt, any compound being soluble in a used solvent may be possible (e.g. acetates, carbonates, acetate tetrahydrates and bromides). It is prefer to have the atomic weight ratio of nickel/manganese in the range of 0.01–1. If the weight ratio is higher which means more amount of nickel than preferred is used, the other catalyst compounds could not act as the catalyst.

Reaction gas used in the present invention is an oxygen or a mixture gas of oxygen and inert gas such as nitrogen. Amount of oxygen is in the range of 2–75% (v/v) to the total gas amount. Carbon dioxide is also used to activate the reaction efficiency in the range of 1–90% (v/v) to the total gas amount, preferably 10–85% (v/v). If the amount of carbon dioxide is used less than 1% (v/v), it is impossible to obtain the desired effect. On the other hand, if it is used more than 90% (v/v), it is impossible to perform smooth oxidation due to low concentration of oxygen. The carbon dioxide is applied periodically or continually in the vapor or liquid reaction medium. When it is applied into the vapor reaction medium, it is recycled after mixing with fresh gas or reaction waste containing remained oxygen and carbon dioxide.

Aromatic carboxylic acids of the present invention are prepared by batch or continuous process. Preferred temperature is in the range of 100–255° C., more preferably 170–210° C. If the temperature is lower than 100° C., the reaction rate is too slow to be practical. On the other hand, if is higher than 255° C., it is not economical due to side reactions. Reaction pressure is used to keep alkylaromatic compounds, its intermediates, and solvent in partially liquid state and preferably 1–35 atm of gauge pressure, more preferably 8–30 atm.

Now, the invention is described in more detail with reference to the following Examples, to which, however, the invention is not restricted without departing from the spirit and scope thereof.

Example 1 and Comparative Examples 1 to 7 are the preparation of terephthalic acid by oxidation of p-xylene. Reaction efficiencies and yields of terephthalic acid and partially oxidized intermediate (p-toluic acid) are compared.

EXAMPLE 1 p-Xylene, acetic acid and catalyst were placed in 150 ml of titan pressure reactor. Total amount of reactants was 30.42 g and the ratio of p-xylene and acetic acid was 17:83. Each amount was 899 ppm for cobalt, 1170 ppm for manganese and 2990 ppm for bromine in cobalt/manganese/bromine complex catalyst based to the total weight of reactants. Cobalt bromide was used for sources of cobalt and bromine. Manganese acetate tetrahydrate was used as a source of manganese. 163 ppm of nickel was used based on the total weight of reactants and nickel acetate tetrahydrate was used as a source of nickel. The reaction mixture was stirred under nitrogen atmosphere and heated to 170° C. 50% of nitrogen gas and 33.3% of carbon dioxide gas were applied and 16.7% of oxygen gas was then applied instantaneously into the reaction mixture. The pressure was applied to be total gauge pressure of 12 and fresh oxygen was continually applied for consumed amount. The reaction mixture was reacted for 180 min and then cooled. The oxide product was collected and dried. The reaction condition, consumed amount of oxygen, and yield of each terephthalic acid and p-toluic acid were summarized in Table 1. When Example 1 was compared to Comparative Example 3 wherein carbon dioxide and nickel were not used, the reaction efficiency of Example 1 was improved 16.9% and the formation of the desired product terephthalic acid was remarkably increased. Further when Example 1 was compared to Comparative Example 1 wherein only carbon dioxide was used, the reaction efficiency was similar by using nickel but the selectivity toward the formation of terephthalic acid was much higher than that of Comparative Example 1. When Example 1 was compared to Comparative Examples 1 and 2, in which either carbon dioxide or nickel was added, and Comparative Example 3, in which either carbon dioxide or nickel was not added, the increment of the yield of terephthalic acid in Example 1 is much higher than the sum of each increment of Comparative Examples 1 and 2, clearly exhibiting a synergistic effect.

Comparative Example 1

The reaction was performed in the same manner as Example 1 but without addition of nickel. The reaction condition, consumed amount of oxygen, and yield of each terephthalic acid and p-toluic acid were summarized in Table 1. When Comparative Example 1 was compared to Comparative Example 3 wherein carbon dioxide and nickel were not used, the reaction efficiency of Comparative Example 1 was improved 16.8% and the formation of the desired product terephthalic acid was also increased.

Comparative Example 2

The reaction was performed in the same manner as Example 1 but without addition of carbon dioxide. The reaction condition, consumed amount of oxygen, and yield of each terephthalic acid and p-toluic acid were summarized in Table 1. When Comparative Example 2 was compared to Comparative Example 3 wherein carbon dioxide and nickel were not used, the reaction efficiency of Comparative Example 2 was similar but the formation of the desired product terephthalic acid was increased.

Comparative Example 3

The reaction was performed in the same manner as Example 1 but without addition of carbon dioxide and nickel. Therefore 83.3% of nitrogen and 16.7% of oxygen were applied into the reaction mixture. The reaction condition, consumed amount of oxygen, and yield of each terephthalic acid and p-toluic acid were summarized in Table 1. Both reaction efficiency and formation of the desired product terephthalic acid was considerably low.

Comparative Example 4

The reaction was performed in the same manner as Example 1 except that the reaction was performed for 120 min instead of 180 min. The reaction condition, consumed amount of oxygen, and yield of each terephthalic acid and p-toluic acid were summarized in Table 1. When Comparative Example 4 was compared to Comparative Example 5 wherein only carbon dioxide was not used, the reaction efficiency was increased 46.5% and the formation of the desired product terephthalic acid was also increased.

Comparative Example 5

The reaction was performed in the same manner as Example 4 but without addition of carbon dioxide and nickel. Therefore 83.3% of nitrogen and 16.7% of oxygen were applied into the reaction mixture. The reaction condition, consumed amount of oxygen, and yield of each terephthalic acid and p-toluic acid were summarized in Table 1. Both reaction efficiency and formation of the desired product terephthalic acid was considerably low.

Comparative Example 6

The reaction was performed in the same manner as Example 1 except that the reaction was performed for 60 min instead of 180 min. The reaction condition, consumed amount of oxygen, and yield of each terephthalic acid and p-toluic acid were summarized in Table 1. When Comparative Example 6 was compared to Comparative Example 7 wherein only carbon dioxide was not used, the reaction efficiency was increased 11.7% and the formation of the desired product terephthalic acid was also increased.

Comparative Example 7

The reaction was performed in the same manner as Example 6 but without addition of carbon dioxide and nickel. Therefore 83.3% of nitrogen and 16.7% of oxygen were applied into the reaction mixture. The reaction condition, consumed amount of oxygen, and yield of each terephthalic acid and p-toluic acid were summarized in Table 1. Both reaction efficiency and formation of the desired product terephthalic acid was considerably low.

TABLE 1

| Category | | Temp. (° C.) | Time (min) | $CO_2$ (%) | Nickel (ppm) | Consumed Oxygen (mmol)* | Yield (mole %) Terephthalic acid | p-toluic acid |
|---|---|---|---|---|---|---|---|---|
| Ex. | 1 | 170 | 180 | 33.3 | 163 | 97.5 | 56.2 | 31.2 |
| Comp. | 1 | 170 | 180 | 33.3 | 0 | 97.5 | 34.8 | 36.9 |
| Ex. | 2 | 170 | 180 | 0 | 163 | 83.7 | 25.2 | 40.9 |
| | 3 | 170 | 180 | 0 | 0 | 83.4 | 17.7 | 47.9 |
| | 4 | 170 | 120 | 33.3 | 0 | 67.7 | 19.4 | 28.2 |
| | 5 | 170 | 120 | 0 | 0 | 46.2 | 3.1 | 31.0 |
| | 6 | 170 | 60 | 33.3 | 0 | 42.8 | 2.2 | 28.4 |
| | 7 | 170 | 60 | 0 | 0 | 38.3 | 0.4 | 23.3 |

*Theoretical oxygen equivalent: 145.8 mmol

In Example 2 and Comparative Examples 8 to 10 preparing terephthalic acid from p-xylene, the reaction time was compared to consume the same amount of oxygen.

EXAMPLE 2

The reaction was performed in the same manner as Example 1 except that a reaction temperature was 190° C. and a gauge pressure was 20 atm. 25% of oxygen, 30% of carbon dioxide and 45% of nitrogen were applied. When 85% of theoretical oxygen equivalent was consumed, the reaction was completed. The reaction time was 54 min which was decreased of 50% compared with that of Comparative Example 10 wherein carbon dioxide and nickel were not used. The amount of consumed oxygen was measured over the reaction time wherein a consuming rate of oxygen was rapidly increased in the initial stage. The formation of terephthalic acid was high. That is, when carbon dioxide and nickel were used, both the reaction efficiency and the formation of terephthalic acid were improved due to reduced formation of side product.

Comparative Example 8

The reaction was performed in the same manner as Example 2 but without addition of nickel. The time to consume 85% of theoretical oxygen equivalent was 84 min.

The reaction time was decreased, and the consuming rate of oxygen and the formation of terephthalic acid were increased compared with those of Comparative Example 10 wherein carbon dioxide and nickel were not used.

Comparative Example 9

The reaction was performed in the same manner as Example 2 but without addition of carbon dioxide. The time to consume 85% of theoretical oxygen equivalent was 90 min. The reaction time was decreased, and the consuming rate of oxygen and the formation of terephthalic acid were increased compared with those of Comparative Example 10 wherein carbon dioxide and nickel were not used.

Comparative Example 10

The reaction was performed in the same manner as Example 2 but without addition of carbon dioxide and nickel. Therefore, 25% of oxygen and 75% of nitrogen were applied into the reaction mixture. The time to consume 85% of theoretical oxygen equivalent was 110 min. The formation of terephthalic acid was the lowest compared with other Example 2 and Comparative Examples 8 and 9.

with Comparative Example 13 wherein carbon dioxide and nickel were not used.

Comparative Example 11

The reaction was performed in the same manner as Example 3 but without addition of nickel. 95.7 mmol of oxygen was consumed for 60 min. Both reaction efficiency and formation of isophthalic acid were increased compared with Comparative Example 13 wherein carbon dioxide and nickel were not used.

Comparative Example 12

The reaction was performed in the same manner as Example 3 but without addition of carbon dioxide and nickel. 95.4 mmol of oxygen was consumed for 60 min. Both reaction efficiency and formation of isophthalic acid were slightly increased compared with Comparative Example 13 wherein carbon dioxide and nickel were not used.

TABLE 2

| Category | | Temp. (° C.) | Time (min)* | $CO_2$ (%) | Nickel (ppm) | Consumed oxygen (mmol)** | | | Yield (mol %) | |
|---|---|---|---|---|---|---|---|---|---|---|
| | | | | | | 15 min | 30 min | 45 min | Terephthalic acid | p-toluic acid |
| Ex. | 2 | 190 | 54 | 30.0 | 163 | 37.8 | 80.6 | 109.1 | 86.3 | 0.8 |
| Comp. | 8 | 190 | 84 | 30.0 | 0 | 35.1 | 68.1 | 91.1 | 85.4 | 0.0 |
| Ex. | 9 | 190 | 90 | 0 | 163 | 35.8 | 69.0 | 96.3 | 84.7 | 0.3 |
| | 10 | 190 | 110 | 0 | 0 | 20.5 | 53.3 | 77.4 | 82.7 | 3.8 |

*Time to consume 85% of theoretical oxygen equivalent where the reaction was completed)
**Theoretical oxygen equivalent 145.8 mmol In Example 3 and Comparative Examples 11–13 preparing terephthalic acid from m-xylene, yield and reactivity were compared.

EXAMPLE 3

The reaction was performed in the same manner as Example 2 except that m-xylene was used and reaction was performed for 60 min. 98.9 mmol of oxygen was consumed for 60 min. The reaction efficiency was increased 4.1% and formation of isophthalic acid was also increased compared Comparative Example 13

The reaction was performed in the same manner as Example 2 but without addition of nickel. Therefore, 25% of oxygen and 75% of nitrogen were applied into the reaction mixture. 95.0 mmol of oxygen was consumed for 60 min. Both reaction efficiency and formation of isophthalic acid were the lowest compared with other Example 3 and Comparative Examples 11 and 12.

TABLE 3

| Category | | Temp. (° C.) | Time (min) | $CO_2$ (%) | Nickel (ppm) | Consumed Oxygen (mmol)** | Yield (mol %) | |
|---|---|---|---|---|---|---|---|---|
| | | | | | | | Terephthalic acid | p-toluic acid |
| Ex. | 3 | 190 | 60 | 30.0 | 163 | 98.9 | 54.9 | 21.4 |
| Comp. | 11 | 190 | 60 | 30.0 | 0 | 95.7 | 53.0 | 17.2 |
| Ex. | 12 | 190 | 60 | 0 | 163 | 95.4 | 51.1 | 17.3 |
| | 13 | 190 | 60 | 0 | 0 | 95.0 | 50.4 | 10.4 |

**Theoretical oxygen equivalent: 145.8 mmol

As described above, it was noted that in the preparation of aromatic carboxylic acids from alkylaromatics by oxidation in acetic acid as solvent with oxygen-containing gas in the presence of cobalt/manganese/bromine complex catalyst, the use of nickel and carbon dioxide in an appropriate amount increases an activity of cobalt/manganese/bromine complex catalyst. Especially nickel has a synergistic effect with carbon dioxide and maximize the formation of the desired product having the corresponding carboxylic groups to the number of alkyl groups in a reactant.

What is claimed is:

1. A process for preparing aromatic carboxylic acids, comprising the steps of:
    conducting a liquid-phase oxidation with oxygen-containing gas of alkylaromatics and partial oxidized intermediates thereof,
    conducting said oxidation step in the presence of:
        a cobalt/manganese/bromine complex catalyst;
        a solvent of acetic acid;
        nickel; and
        carbon dioxide.

2. The process for preparing aromatic carboxylic acids according to claim 1, wherein the atomic weight ratio of said nickel/manganese is in the range of 0.01 to 1.

3. The process for preparing aromatic carboxylic acids according to claim 1, wherein the applied amount of said oxygen is in the range of 2 to 75% (v/v) relative to the total gas amount.

4. The process for preparing aromatic carboxylic acids according to claim 1, wherein the applied amount of said carbon dioxide is in the range of 1 to 90% (v/v) relative to the total gas amount.

5. The process for preparing aromatic carboxylic acids according to claim 1, wherein said alkylaromatic is selected from the group consisting of toluene, o-xylene, m-xylene, p-xylene, pseudocumene (1,2,4-trimethylbenzene), mesitylene (1,3,5-trimethylbenzene), durene (2,3,5,6-tetramethylnaphthalene), methylnaphthalene, 2,6-dimethylnaphthalene and 4,4'-dimethylbiphenyl.

6. The process for preparing aromatic carboxylic acids according to claim 1, wherein said aromatic carboxylic acid is selected from the group consisting of benzoic acid, phthalic acid, isophthalic acid, terephthalic acid, trimellitic acid, trimesic acid, pyromellitic acid, carboxylnaphthalic acid, 2,6-dicarboxynaphthalic acid and 4,4'-dicarboxybiphenylic acid.

7. The process for preparing aromatic carboxylic acids according to claim 1, wherein said carbon dioxide is periodically or continually applied in vapor- or liquid-phase.

8. The process for preparing aromatic carboxylic acids according to claim 7, wherein said carbon dioxide is recycled after mixing with fresh gas or reaction waste containing remained oxygen and carbon dioxide, when it is applied in vapor-phase.

* * * * *